(12) United States Patent
Kapur et al.

(10) Patent No.: US 9,056,191 B2
(45) Date of Patent: Jun. 16, 2015

(54) APPARATUS AND METHOD FOR REMOVING OCCLUSIVE TISSUE

(75) Inventors: Terri Kapur, Sharon, MA (US); Arnaz Malhi, Watertown, MA (US); Sean Pruitt, Franklin, MA (US)

(73) Assignee: Covidien LP, Mansfield, MA (US)

( * ) Notice: Subject to any disclaimer, the term of this patent is extended or adjusted under 35 U.S.C. 154(b) by 391 days.

(21) Appl. No.: 13/444,034

(22) Filed: Apr. 11, 2012

(65) Prior Publication Data

US 2013/0274728 A1 Oct. 17, 2013

(51) Int. Cl.
*A61M 25/10* (2013.01)

(52) U.S. Cl.
CPC ................................ *A61M 25/1011* (2013.01)

(58) Field of Classification Search
None
See application file for complete search history.

(56) References Cited

U.S. PATENT DOCUMENTS

| | | | |
|---|---|---|---|
| 4,636,195 A | 1/1987 | Wolinsky | |
| 4,762,128 A * | 8/1988 | Rosenbluth | 606/192 |
| 4,976,711 A | 12/1990 | Parins et al. | |
| 5,226,889 A | 7/1993 | Sheiban | |
| 5,462,529 A | 10/1995 | Simpson et al. | |
| 5,653,684 A | 8/1997 | Laptewicz et al. | |
| 5,695,498 A * | 12/1997 | Tower | 606/108 |
| 5,833,650 A | 11/1998 | Imran | |
| 5,868,708 A * | 2/1999 | Hart et al. | 604/104 |
| 5,904,711 A | 5/1999 | Flom et al. | |
| 5,947,985 A | 9/1999 | Imran | |
| 6,015,420 A | 1/2000 | Wulfman et al. | |
| 6,063,069 A | 5/2000 | Cragg et al. | |
| 6,096,054 A | 8/2000 | Wyzgala et al. | |
| 6,126,635 A | 10/2000 | Simpson et al. | |
| 6,135,991 A | 10/2000 | Muni et al. | |
| 6,156,048 A | 12/2000 | Wulfman et al. | |
| 6,203,561 B1 | 3/2001 | Ramee et al. | |
| 6,258,061 B1 | 7/2001 | Drasler et al. | |
| 6,258,109 B1 | 7/2001 | Barry et al. | |
| 6,273,876 B1 | 8/2001 | Klima et al. | |

(Continued)

FOREIGN PATENT DOCUMENTS

| | | |
|---|---|---|
| CN | 2049956 U | 12/1989 |
| CN | 1867299 A | 11/2006 |

(Continued)

OTHER PUBLICATIONS

European Search Report dated Aug. 7, 2013 from corresponding EP Application No. 13162961.0. (8 pgs.).

(Continued)

*Primary Examiner* — Kennedy Schaetzle

(74) *Attorney, Agent, or Firm* — Thomas M. Johnston, Esq.

(57) ABSTRACT

A tissue treatment apparatus for restoring patency in a body vessel is provided. The tissue treatment apparatus includes an elongated catheter dimensioned for insertion within a body vessel having an at least partial occlusion. Proximal and distal expandable segments are mounted to the elongated catheter and are positionable adjacent the occlusion and are configured to transition from a first condition to a second expanded condition. A mesh in operative engagement with the proximal and distal expandable segments is expandable radially outwardly from the catheter upon corresponding transition of the proximal and distal expandable segments to the second condition. The mesh includes a conductive material adapted to transmit electrosurgical energy to treat and facilitate removal of the occlusion, to thereby assist in restoring patency within the body vessel.

18 Claims, 3 Drawing Sheets

(56) References Cited

U.S. PATENT DOCUMENTS

| | | |
|---|---|---|
| 6,290,689 B1 | 9/2001 | Delaney et al. |
| 6,299,623 B1 | 10/2001 | Wulfman |
| 6,416,526 B1 | 7/2002 | Wyzgala et al. |
| 6,419,673 B1 | 7/2002 | Edwards et al. |
| 6,451,037 B1 | 9/2002 | Chandrasekaran et al. |
| 6,454,741 B1 | 9/2002 | Muni et al. |
| 6,482,216 B1 | 11/2002 | Hiblar et al. |
| 6,485,500 B1 | 11/2002 | Kokish et al. |
| 6,491,660 B2 | 12/2002 | Guo et al. |
| 6,503,261 B1 | 1/2003 | Bruneau et al. |
| 6,544,276 B1 | 4/2003 | Azizi |
| 6,569,146 B1 | 5/2003 | Werner et al. |
| 6,569,177 B1 | 5/2003 | Dillard et al. |
| 6,579,299 B2 | 6/2003 | McGuckin, Jr. et al. |
| 6,595,953 B1 | 7/2003 | Coppi et al. |
| 6,616,657 B2 | 9/2003 | Simpson et al. |
| 6,632,230 B2 | 10/2003 | Barry |
| 6,635,027 B1 | 10/2003 | Cragg et al. |
| 6,685,718 B1 | 2/2004 | Wyzgala et al. |
| 6,814,712 B1 | 11/2004 | Edwards et al. |
| 6,818,001 B2 | 11/2004 | Wulfman et al. |
| 6,884,257 B1* | 4/2005 | Cox ............... 623/1.11 |
| 6,893,438 B2 | 5/2005 | Hall et al. |
| 6,932,776 B2 | 8/2005 | Carr |
| 6,984,239 B1 | 1/2006 | Drasler et al. |
| 6,997,925 B2 | 2/2006 | Maguire et al. |
| 7,410,486 B2 | 8/2008 | Fuimaono et al. |
| 7,429,261 B2 | 9/2008 | Kunis et al. |
| 8,696,621 B2* | 4/2014 | Gunday et al. ............ 604/96.01 |
| 2001/0000350 A1* | 4/2001 | Durcan et al. ............ 623/1.11 |
| 2002/0029031 A1* | 3/2002 | Bagaoisan et al. ............ 604/509 |
| 2002/0198521 A1 | 12/2002 | Maguire |
| 2004/0236412 A1* | 11/2004 | Brar et al. ............ 623/1.31 |
| 2006/0041300 A1* | 2/2006 | Zhang et al. ............ 607/126 |
| 2008/0161801 A1 | 7/2008 | Steinke et al. |
| 2009/0248059 A1 | 10/2009 | Morsi |
| 2011/0046542 A1 | 2/2011 | Evans et al. |
| 2011/0082483 A1 | 4/2011 | Diamant et al. |
| 2011/0152683 A1* | 6/2011 | Gerrans et al. ............ 600/435 |
| 2011/0202098 A1 | 8/2011 | Demarais et al. |
| 2012/0239028 A1 | 9/2012 | Wallace et al. |

FOREIGN PATENT DOCUMENTS

| | | |
|---|---|---|
| CN | 101355909 A | 1/2009 |
| CN | 101588762 A | 11/2009 |
| DE | 10010467 A1 | 9/2001 |
| JP | 7-100214 | 4/1995 |
| JP | 10-230017 | 9/1998 |
| JP | 2003-522560 | 7/2003 |

OTHER PUBLICATIONS

International Search Report on related EP Application No. 13162961.0 from International Searching Authority (EPO) dated Feb. 17, 2014.

International Search Report on related JP Application No. 2013-82012 from International Searching Authority (JIPO) dated Feb. 14, 2014.

Notification of First Office Action, and translation thereof, from Counterpart Chinese Patent Application No. 201310262857.6, dated Nov. 2, 2014, 17 pp.

* cited by examiner

APPARATUS AND METHOD FOR REMOVING OCCLUSIVE TISSUE

BACKGROUND

1. Technical Field

The present disclosure relates to an apparatus and method for removing occlusive tissue within a vessel. More particularly, the present disclosure relates to an endovascular tissue removal apparatus that includes an expandable conductive mesh.

2. Background of Related Art

Apparatus, methods and systems for removing unwanted occlusive tissue located within vessels are known in the art. Certain types of occlusive tissue are more suitable to certain methods of removal. For example, whereas acute clots are amenable to treatment with a thrombolytic agent, such as, for example, tissue plasminogen activator (tPA), chronic clots are not amendable to such treatment and may require treatment using mechanical, electrical, or other occlusive tissue removal apparatus or methods. Although apparatus, methods and systems that utilize both electrosurgical energy and mechanical energy (or combinations thereof) to effect removal of occlusive tissue are known, such devices may not be effective on acute clots, or may cause coagulation or tissue damage. Thus, improvements to the known apparatus and methods are desirable to enable a device that may be effective with both chronic and acute clots, and the entire spectrum in between.

Accordingly, there exists a need in the art for an improved apparatus and method for removing and/or dispersing different types of occlusive tissue from vessels.

SUMMARY

The present disclosure provides a tissue treatment apparatus for restoring patency in a body vessel. The tissue treatment apparatus includes an elongated catheter dimensioned for insertion within a body vessel having an at least partial occlusion. The elongated catheter defines a longitudinal axis and having proximal and distal ends. Proximal and distal expandable segments are mounted to the elongated catheter and are positionable adjacent the occlusion. The proximal and distal expandable segments adapted to transition from a first contracted condition to a second expanded condition. A mesh in operative engagement with the proximal and distal expandable segments is expandable radially outwardly from the catheter upon corresponding transition of the proximal and distal expandable segments to the second expanded condition. The mesh includes a conductive material adapted to transmit electrosurgical energy to treat and facilitate removal of the occlusion, to thereby assist in restoring patency within the body vessel.

In embodiments, an electrosurgical energy source is in electrical communication with the mesh. In certain instances, the electrosurgical energy transmitted is either radio-frequency (RF) energy or microwave energy. In embodiments, the mesh is dimensioned and adapted to function in a monopolar mode of operation. An electrical conductor extends along at least a portion of a longitudinal length of the catheter and is in electrical communication with the mesh.

In embodiments, the mesh defines a generally hourglass shape when proximal and distal expandable segments are in the second expanded condition.

In embodiments, the proximal and distal expandable segments are dimensioned to engage an interior wall of the body vessel in the second expanded condition. A least an intermediate mesh segment of the mesh is spaced from the interior wall of the body vessel when the proximal and distal expandable segments are in the expanded operative condition. In embodiments, the first and second expandable segments are balloons, and wherein the catheter includes a fluid channel in fluid communication with the proximal and distal balloons to facilitate the transition of the proximal and distal balloons from the first contracted condition to the second expanded condition.

In certain embodiments, the catheter defines a secondary channel dimensioned to convey negative pressure and at least one aperture in fluid communication with the secondary channel and the area adjacent the mesh to assist in aspirating material from adjacent the occlusion. The secondary channel may be dimensioned to convey treatment fluids for emission from the at least one aperture.

In embodiments, a maximum outer diameter of the proximal and distal expandable segments is greater than a maximum outer diameter of the conductive mesh to prevent the conductive mesh from contacting the body vessel.

The present disclosure also provides a method for restoring patency in a body vessel. An elongated catheter is advanced within a body vessel to a location adjacent an at least partial occlusion within the body vessel. The elongated catheter defines proximal and distal ends. Subsequently, proximal and distal expandable segments of the elongated catheter are positioned adjacent the occlusion. The proximal and distal expandable segments have a conductive mesh operatively coupled thereto. Thereafter, the proximal and distal expandable segments are expanded to radially expand the conductive mesh to a predetermined relation with respect to the occlusion. In certain embodiments, when the proximal and distal expandable segments are expanded, the conductive mesh may be positioned in spaced relation with respect to the occlusion.

Electrosurgical energy may then be delivered to the conductive mesh whereby the conductive mesh transmits the electrosurgical energy to cause at least partial treatment of the occlusion to thereby restore patency to the body vessel. The treatment may be by ablation, breaking, remodeling (e.g., melting) or dispersion of the occlusion.

In certain embodiments, the treated occlusion particles may be removed through the elongated catheter. In this instance, the occlusion particles may be directed through an aperture in the elongated catheter and within a channel of the elongated catheter under negative pressure.

In embodiments, the proximal and distal expandable segments are balloons and wherein the step of expanding includes introducing fluid into the balloon segments.

BRIEF DESCRIPTION OF THE DRAWINGS

Various embodiments of the presently disclosed endovascular tissue removal device are described herein with reference to the drawings wherein.

DESCRIPTION OF THE EMBODIMENTS

Figure 1:
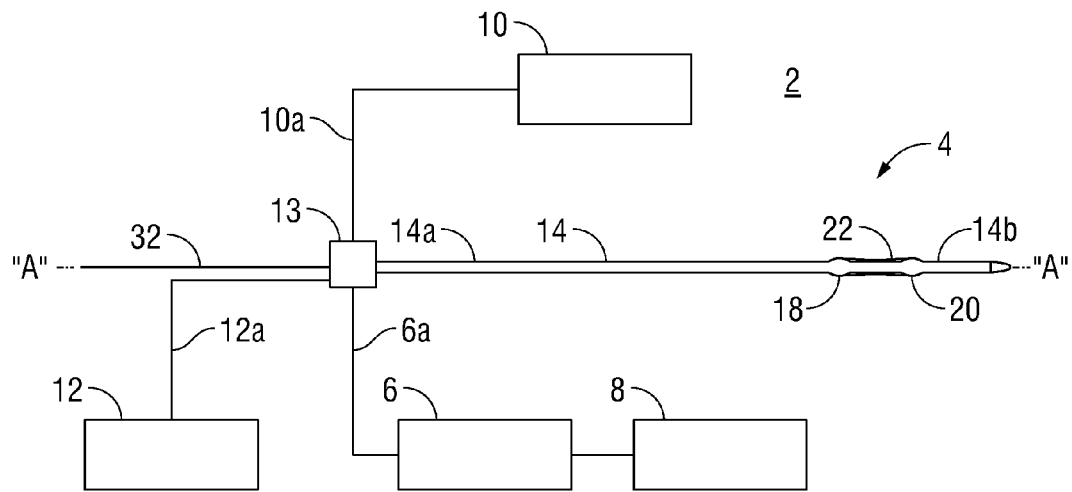
FIG. 1 is a schematic view of a monopolar electrosurgical system including one embodiment of the presently disclosed endovascular tissue removal apparatus.

Embodiments of the presently disclosed endovascular tissue removal device will now be described in detail with reference to the drawings wherein like reference numerals identify similar or identical elements. As used herein, the term "distal" refers to that portion of the device which is furthest from the user while the term "proximal" refers to that portion of the device which is closer to the user. In the following description, well known functions or constructions are not described in detail to avoid obscuring the present disclosure in unnecessary detail.

FIG. 1 is a schematic illustration of a monopolar electrosurgical system 2 including one embodiment of the presently disclosed endovascular tissue removal device 4 according to the present disclosure. The system 2 includes an endovascular tissue removal apparatus 4, an electrosurgical generator 6, a ground pad 8, a pressurized source of fluid 10, and a fluid suction device 12.

Continuing with reference to FIG. 1, the electrosurgical generator 6 is configured to provide electrosurgical energy, such as, for example, radio frequency (RF) energy to the tissue removal apparatus 4. The transmitted energy from the tissue removal apparatus 4 is directed back to the electrosurgical generator 6 via the ground pad 8 that is positioned in contact with a patient. In certain instances, the electrosurgical generator 6 may be configured to provide microwave or other forms of energy including heat.

With reference also to FIGS. 2-4B, the tissue removal apparatus 4 includes an elongated catheter 14 having proximal and distal expandable segments 18 and 20, respectively, and a conductive mesh 22 (FIG. 5) operably coupled between the proximal and distal expandable segments 18 and 20. In one embodiment, the proximal and distal expandable segments 18 and 20 include proximal and distal balloons Catheter 14 is dimensioned for insertion within a body vessel and defines a longitudinal axis "A-A" and has proximal and distal ends, 14a and 14b, respectively (FIG. 1). Catheter 14 may be formed from a synthetic resin, such as a polyurethane or similar material. Alternatively, catheter 14 may be formed from a softer elastomeric material such as silicone. The assembled catheter 14 should have sufficient pliability to be insertable into a body vessel, yet be sufficiently rigid to be capable of applying pressure on a vessel occlusion.

Proximal end 14a of catheter 14 includes a hub 13 (FIG. 1) having a plurality of ports (not shown in detail) that are adapted to be coupled to conduits 10a and 12a which interconnect catheter 14 and pressurized source of fluid 10, and fluid suction device 12, respectively. In addition, hub 13 also includes a connector (not explicitly shown) adapted to receive a wire or cable 6a for electrically connecting electrosurgical generator 6 to catheter 14.

A fluid channel 16 (FIG. 3) may be positioned between inner and outer walls of catheter 14 and extends along a length of catheter 14 to provide pressurized fluid, such as, for example, saline, water, contrast agent, or air to proximal and distal expandable segments 18 and 20. In one embodiment, a single channel 16 communicates with both the proximal and distal expandable segments 18 and 20 such that proximal and distal expandable segments 18 and 20 can be simultaneously inflated or deflated. Alternately, a pair of channels 16 may be provided, wherein each communicates with one of the proximal and distal expandable segments 18 and 20 to enable the proximal and distal expandable segments 18 and 20 to be independently inflated and deflated.

Referring again to FIG. 2, proximal expandable segment 18 and distal expandable segment 20 may be operably mounted in spaced relation to the distal end 14b of the catheter 14 via one or more suitable coupling methods, such as, for example, using welding, adhesives, overmolding, or the like. Radio-opaque markers (not shown) may be located on the expandable segments 18, 20, or on the catheter 14 to enable the clinician to properly position the tissue removal apparatus 4.

Figure 2:
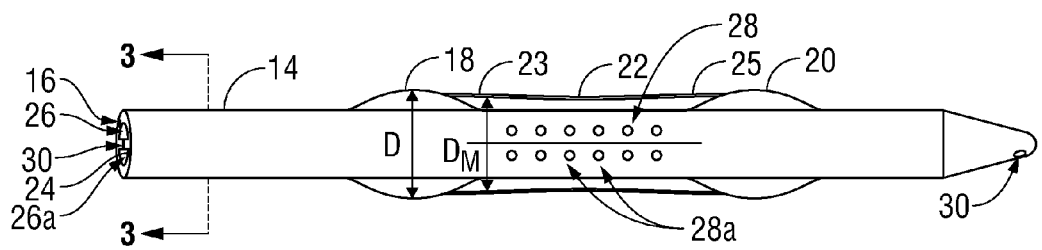
FIG. 2 is an enlarged, side cross-sectional view of a distal end of the endovascular tissue removal apparatus shown in FIG. 1.
Figure 3:
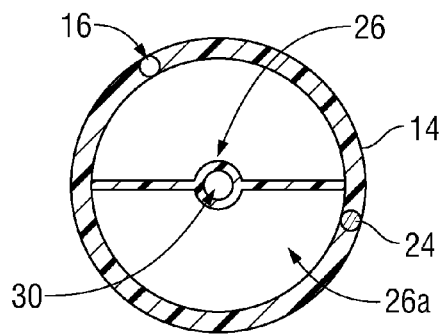
FIG. 3 is a cross-sectional view taken along section lines 3-3 of FIG. 2.
Figure 4A:
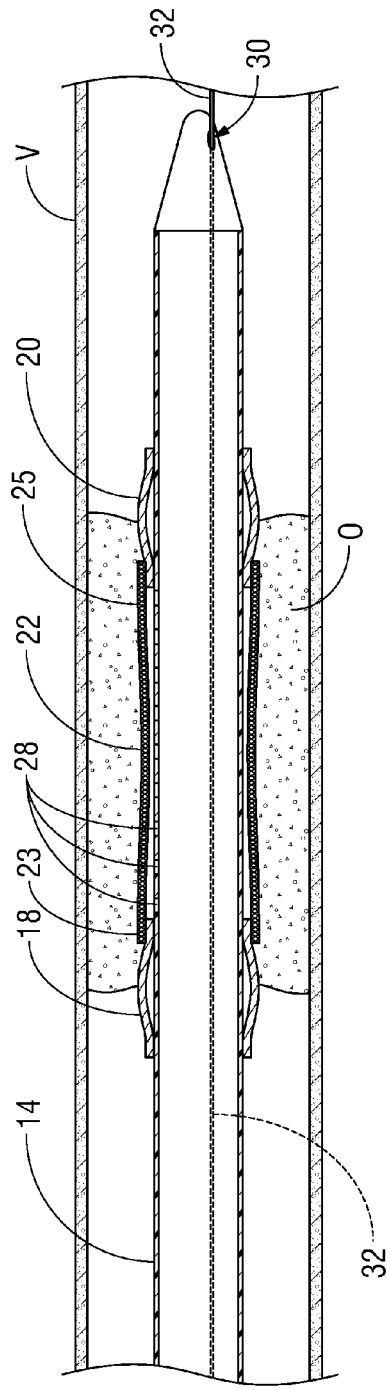
FIGS. 4A and 4B are side, cross-sectional views of the distal end of the endovascular tissue removal apparatus shown in FIG. 2 positioned within a vessel and illustrated in an activated and deactivated configuration, respectively.
Figure 4B:
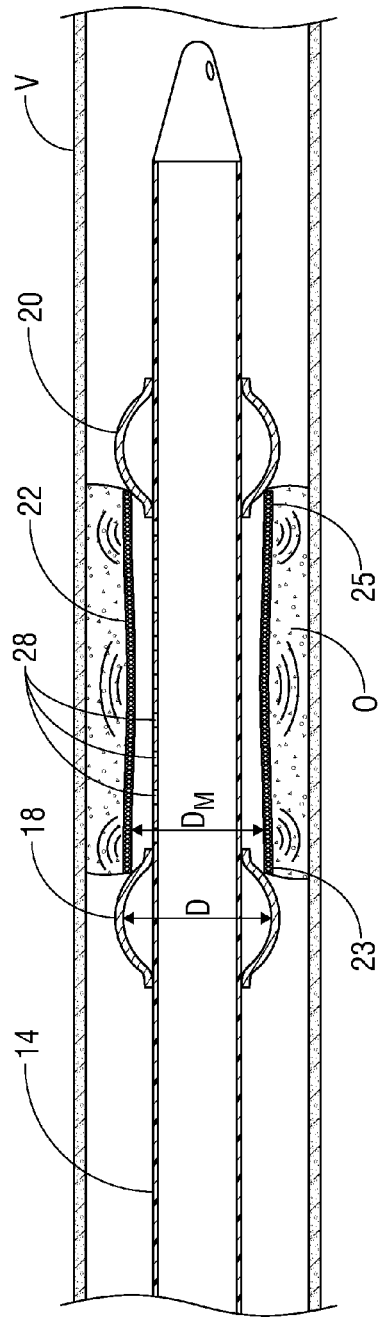

Proximal and distal expandable segments 18 and 20 communicate with the source of pressurized fluid 10 via the channel 16 to facilitate transitioning of the proximal and distal expandable segments 18 and 20 from a first contracted state (FIG. 4A), to a second expanded state (FIG. 4B). In the expanded state, the conductive mesh 22, which is supported between the proximal and distal expandable segments 18 and 20, is moved radially outwardly into contact with an occlusion "O" (FIG. 4B). The force of the conductive mesh 22 on the occlusion "O" may be altered by inflating or deflating expandable segments 19 and 20. In the expanded state, the proximal and distal expandable segments 18 and 20 center the catheter 14 within a vessel "V" to center the conductive mesh 22 within the vessel "V". By centering the conductive mesh 22 within a vessel, the spacing between the conductive mesh 22 and a vessel wall may be controlled to prevent inadvertent damage to the vessel wall. In some embodiments, a spacing of 1.5 mm to about 2 mm between conductive mesh 22 and the vessel wall is desired to prevent damage to the vessel wall. The conductive mesh 22 may be attached to the proximal and distal expanding segments 18 and 20 at a point along the catheter 14 such that the conductive mesh 22 would not touch the vessel "V" in the expanded state, such as shown in FIG. 2. In other words, as the proximal and distal expanding segments 18 and 20 expand, the maximum outer diameter "D" of the expanded segments 18 and 20 is greater than the maximum outer diameter "$D_M$" of the conductive mesh 22.

In one embodiment, the conductive mesh 22 is secured to respective outer surfaces of the proximal and distal expandable segments 18 and 20 via a curable adhesive that is configured to withstand the high temperatures that may be present at a surgical site as the conductive mesh 22 is activated and transmitting electrosurgical energy to treat tissue. Alternately, other securement methods, such as ultrasonic welding, may be used to secure the conductive mesh 22 to the expandable segments 18 and 20.

Figure 5:
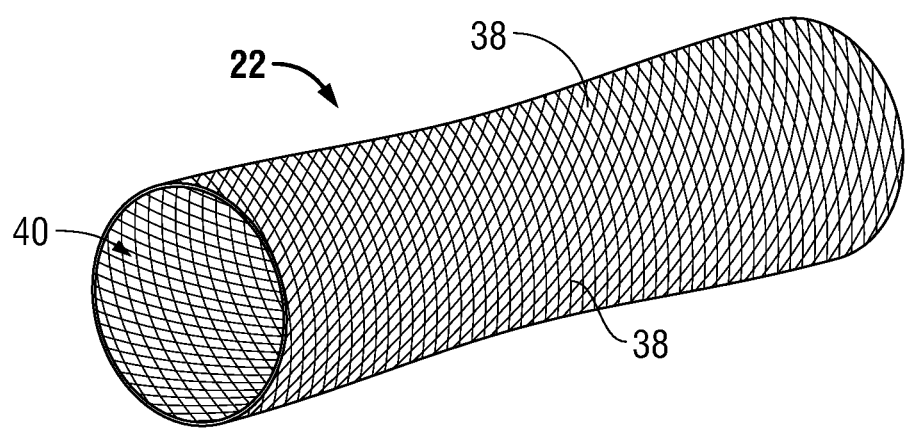
FIG. 5 is a side perspective view of a conductive mesh of the endovascular tissue removal apparatus.

Conductive mesh 22 may have any suitable configuration and may be made from any suitable conductive material that enables the conductive mesh 22 to move from its normally contracted configuration (FIG. 4A) to its expanded configuration (FIG. 4B) to treat and facilitate removal of the occlusion "O", to thereby assist in restoring patency within a body vessel "V". In one embodiment, the conductive mesh 22 is formed from a plurality of stainless steel strands 38 which are connected or woven to one another to provide a semi-permeable barrier including a plurality of interstices 40 (FIG. 5). The plurality of interstices 40 is disposed between the connected strands 38 of stainless steel to provide passageways for fluids and debris to flow from adjacent the occlusion "O" into catheter 14, as will be discussed in further detail below. The plurality of stainless steel strands may be configured such that electrosurgical energy is transmitted throughout the entire conductive mesh 22. Alternatively, only a predetermined portion of the conductive mesh 22 may be configured to transmit electrosurgical energy. In this instance, for example, one or more of the stainless steel strands 38 may be covered with an insulative material or formed entirely of an insulative material. This configuration may prove useful when the electrosurgical energy needs to be directed to a specific area of the occlusive tissue within a vessel or if the occlusive tissue "O" is concentrated on one side of the vessel "V". However, while the conductive mesh 22 is shown and described as a weave of conductive material, any configuration may be employed. For example, a typical stent structure, such as a laser cut stent, may be used.

Conductive mesh 22 is electrically connected to the generator 6 by an electrical conductor such as a wire 24 (FIG. 3) extending along or through the catheter 14. A proximal end of the electrical conductor 24 is connected to the connector (not shown) on the hub 13 of the catheter 14 which is adapted to communicate with the electrosurgical generator 6.

As discussed above, conductive mesh 22 is configured to move outwardly as the proximal and distal expandable segments 18 and 20 are inflated from their contracted state (FIG. 4A) to their expanded state (FIG. 4B). In particular, when conductive mesh 22 is positioned through a vessel occlusion "O", expansion of the proximal and distal expandable segments 18 and 20 lifts the conductive mesh 22 such that the conductive mesh 22 moves closer to or in contact with the vessel occlusion "O" and is spaced from an interior wall of the vessel "V". In accordance with the present disclosure, electrosurgical energy is transmitted to the conductive mesh 22 and transmitted to the occlusion "O" to break up or disperse the occlusion "O" into smaller particles that pass through the plurality of interstices 40 of the conductive mesh 22 for subsequent removal thereof from the surgical site. While the conductive mesh 22 has been described as being expandable by the proximal and distal expandable segments 18 and 20, the conductive mesh 22 may be self-expanding. In such an embodiment, the proximal and distal expandable segments 18 and 20 may be used to constrain the conductive mesh 22 along the longitudinal axis of the catheter 14 and/or further urge the conductive mesh 22 into engagement with the occlusion "O". In embodiments where the conductive mesh 22 is self-expanding, the conductive mesh may or may not be attached to the proximal and distal expandable segments 18 and 20.

In certain embodiments, the catheter 14 may be configured to aspirate the dispersed vessel occlusion "O" that has been electrosurgically treated by the conductive mesh 22. In one embodiment, a secondary or aspiration channel 26 of suitable dimension is in fluid communication with the fluid suction device 12. The aspiration channel 26 is in communication with one or more apertures 28 which extend through the catheter 14 (FIGS. 2 and 4A and 4B) between proximal and distal expandable segments 18 and 20. The aspiration channel 26 is dimensioned to convey negative pressure to assist in aspirating dispersed particles of an occlusion "O" through the apertures 28 and into the aspiration channel 26. The aspiration channel 26 and apertures 28 are configured to enable passage of the dispersed particles therethrough to remove them from the surgical site. In particular, the dispersed particles of the occlusion "O" fall or pass through the plurality of interstices 40 of the conductive mesh 22 and are sucked into the apertures 28, carried away through the aspiration channel 26 and to the fluid suction device 12.

In embodiments, a guidewire 32 (FIG. 1) may be utilized to facilitate positioning the catheter 14 adjacent a vessel occlusion. In this instance, a guidewire bore 30 (FIGS. 3 and 4A) extends through the catheter 14 from the proximal end 14a thereof to the distal end 14b thereof and is configured to receive the guidewire 32 therein. Moreover, and in this instance, hub 13 defines an opening (not shown) which is aligned with guidewire bore 30 to facilitate insertion of a guidewire 32 into guidewire bore 30.

Operation of the monopolar electrosurgical system 2 including the tissue removal apparatus 4 is described in terms of a method for clearing a vessel occlusion "O", such as, for example, a chronic clot within a vessel "V". For illustrative purposes, it is assumed that a guidewire 32 is utilized to position the distal end 14b of the catheter 14 adjacent the vessel occlusion "O".

In use, the guidewire 32 may be positioned within a partially occluded or occluded vessel using, for example, a needle cannula (not shown) in a known manner. In one particular embodiment, the guidewire 32 is utilized to pierce the occlusion "O" to provide a passageway therethrough for the catheter 14. Alternatively, one or more other suitable devices (or methods) may be utilized to provide a passageway through an occlusion "O" which completely obstructs a vessel lumen "V". For example, the catheter 14 may be equipped with a distal tip having a pointed configuration to penetrate the occlusion "O".

Guidewire bore 30 of the catheter 14 may be inserted over the guidewire 32 and the distal end 14b of the catheter 14 may be advanced over the guidewire 32 and positioned adjacent the occlusion "O" (FIG. 4A). In particular, the distal expandable segment 20 may be positioned distal to the occlusion "O", the proximal expandable segment 18 may be positioned proximal to the occlusion "O" and the conductive mesh 22 may be positioned within a passageway through the occlusion "O" (FIG. 4A). Thereafter, guidewire 32 can be removed from catheter 14 (FIG. 4B).

Once in position, the proximal and distal expandable segments 18 and 20 are inflated (FIG. 4B) independently or simultaneously to radially expand the conductive mesh 22 from its contracted configuration to its expanded configuration and to position the conductive mesh 22 close to or in contact with the occlusion "O". The degree of engagement or contact between the conductive mesh 22 and the occlusion "O" can be selectively controlled by the degree of inflation of one or both of the expandable segments 18 and 20. Further, the conductive mesh 22 may be denser in the center to provide greater stiffness in that region. A stiffer center region of the conductive mesh 22 may expand less than the end regions of the conductive mesh 22 to ensure the center region of the conductive mesh 22 does not overly expand and come into contact with the vessel walls, thereby providing greater safety.

Electrosurgical energy is transmitted to and emitted from the conductive mesh 22 to ablate, break up, or disperse the occlusion "O" (FIG. 4B). Under certain surgical scenarios, it may prove useful to move (axially translate and/or rotate) the catheter 14 to reposition the conductive mesh 22 with respect to the occlusion "O". To facilitate the removal of the occlusion "O," the conductive mesh 22 may be provided with a textured, roughened, or sharpened exterior surface that is configured to scrape against the occlusion "O" as the catheter and/or conductive mesh 22 is moved. As the occlusion "O" breaks apart or disperses, the dislodged particles may fall through the plurality of interstices 40 and be drawn into the apertures 28 via suction provided by the fluid suction device 12. When the clinician has completed the procedure, the proximal and distal expanding segments 18 and 20 may be deflated to collapse the conductive mesh 22 around the catheter 14, and the catheter 14 is then removed. In an alternative embodiment, the conductive mesh 22, which may be either expanded by the proximal and distal expanding segments 18 and 20 or self expanding, may be detached from the catheter 14 and left within the vessel "V" to act as a stent against any remaining occlusion "O", thereby providing further patency to the vessel "V". The conductive mesh 22 may be detached by including an electrically detachable link between the wire 24 and the conductive mesh 22, which breaks upon the application of a specific voltage. Such electrically detachable links are known in the art. Further, if the conductive mesh 22 is to be left within the vessel "V", the conductive mesh 22 would not be attached to the proximal and distal expandable segments 18 and 20.

The electrosurgical system 2 disclosed herein enables an end user to effectively remove an occlusion "O" (e.g., a chronic and/or acute clot) in a vessel without the need of chemical agents, such as lytics.

In certain instances, however, a thrombolytic agent, such as, for example, tissue plasminogen activator (tPA) may be used in combination with the system 2 to facilitate removing an occlusion "O" in a vessel "V". In such an embodiment, the aspiration channel 26 may be configured and dimensioned to convey the thrombolytic agent to the plurality of apertures 28 for emission therefrom. Thus, the plurality of apertures 28 may be utilized to deliver the treatment fluid in addition to providing passage for the dispersed particles of the occlusion "O". Alternatively, catheter 14 may define a fluid supply channel 26a which communicates with openings 28a in the catheter 14 to supply treatment fluid between expandable segments 18 and 20 to the occlusion "O", see FIGS. 2 and 3, for example.

While the conductive mesh 22 has been described as applying certain types of electrosurgical energy, for example, RF and/or microwave energy, the conductive mesh 22 may apply other electrosurgical energy or non-electrosurgical energy, such as, for example, mechanical, ultrasonic or resistive heating. The mode of energy utilized should be selected to create a desired effect on the occlusion "O".

Further, while the system 2 has been described as a monopolar system utilizing a ground pad 8 to complete the circuit, other embodiments may include a return electrode on the catheter adjacent the conductive mesh 22. For example, a distal tip of the catheter 14 may include a return electrode operably coupled thereto, or a return electrode may be positioned on the catheter 14 between the proximal and distal expandable segments 18 and 20. In either instance, a second conductor (not shown) similar to that of electrical conductor 24 may extend through the catheter 14 and operably couple to the return electrode to provide a return path for the electrosurgical energy transmitted from the conductive mesh 22 to the occlusion "O". Providing a return electrode on the catheter 14 may prove useful in directing the electrosurgical energy transmitted from the conductive mesh 22 to a specific area of the occlusive tissue within a vessel.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the system based on the above-described embodiments. Accordingly, the present disclosure is not to be limited by what has been particularly shown and described, except as indicated by the appended claims.

The invention claimed is:

1. A tissue treatment apparatus for restoring patency in a body vessel, the tissue treatment apparatus comprising:

an elongated catheter dimensioned for insertion within a body vessel having an at least partial occlusion, the elongated catheter defining a longitudinal axis and having proximal and distal ends;

proximal and distal expandable segments mounted to the elongated catheter and being positionable adjacent the occlusion, the proximal and distal expandable segments being adapted to transition from a first contracted condition to a second expanded condition; and a continuous mesh in operative engagement with the proximal and distal expandable segments, the continuous mesh being expandable radially outwardly from the catheter upon corresponding transition of the proximal and distal expandable segments to the second expanded condition, and the continuous mesh comprising a conductive material adapted to transmit electrosurgical energy to the occlusion; wherein a maximum outer diameter of the proximal and distal expandable segments is greater than a maximum outer diameter of the conductive continuous mesh to prevent the conductive continuous mesh from contacting the body vessel.

2. The tissue treatment apparatus according to claim 1, including an electrosurgical energy source in electrical communication with the continuous mesh.

3. The tissue treatment apparatus according to claim 2, wherein the electrosurgical energy is radio-frequency (RF) energy.

4. The tissue treatment apparatus according to claim 2, wherein the electrosurgical energy is microwave energy.

5. The tissue treatment apparatus according to claim 1, wherein the continuous mesh is dimensioned and adapted to function in a monopolar mode of operation.

6. The tissue treatment apparatus according to claim 1, including an electrical conductor extending along at least a portion of a longitudinal length of the catheter and in electrical communication with the continuous mesh.

7. The tissue treatment apparatus according to claim 1, wherein the continuous mesh defines a generally hourglass shape when the proximal and distal expandable segments are in the second expanded configuration.

8. The tissue treatment apparatus according to claim 1, wherein the proximal and distal expandable segment are dimensioned to engage an interior wall of the body vessel in the second expanded condition, and wherein at least an intermediate mesh segment of the continuous mesh is spaced from the interior wall of the body vessel when the proximal and distal expandable segments are in the second expanded condition.

9. The tissue treatment apparatus according to claim 1, wherein the first and second expandable segments are balloons, and wherein the catheter includes a fluid channel in fluid communication with the proximal and distal balloons to facilitate the transition of the proximal and distal balloons from the first contracted condition to the second expanded condition.

10. The tissue treatment apparatus according to claim 1, wherein the catheter defines a secondary channel dimensioned to convey negative pressure and at least one aperture in fluid communication with the secondary channel and the area adjacent the continuous mesh to assist in aspirating material from adjacent the occlusion.

11. The tissue treatment apparatus according to claim 10, wherein the secondary channel is dimensioned to convey treatment fluids for emission from the at least one aperture.

12. The tissue treatment apparatus according to claim 1, wherein at least a portion of the continuous mesh is configured to be suspended between the proximal and distal expandable segments upon transition of the proximal and distal expandable segments to the second expanded condition.

13. A method for restoring patency in a body vessel, the method comprising the steps of:
    advancing an elongated catheter within a body vessel to a location adjacent an at least partial occlusion within the body vessel, the elongated catheter defining proximal and distal ends;
    positioning proximal and distal expandable segments of the elongated catheter adjacent the occlusion, the proximal and distal expandable segments having a continuous conductive mesh operatively coupled thereto;
    expanding the proximal and distal expandable segments to radially expand the continuous conductive mesh to a predetermined relation with respect to the occlusion;
    delivering electrosurgical energy to the continuous conductive mesh whereby the continuous conductive mesh transmits the electrosurgical energy to the occlusion;
    wherein a maximum outer diameter of the proximal and distal expandable segments is greater than a maximum outer diameter of the continuous conductive mesh to prevent the continuous conductive mesh from contacting the body vessel.

14. The method according to claim 13, including the step of removing treated occlusion particles through the elongated catheter.

15. The method according to claim 14, wherein the step of removing includes directing the occlusion particles through an aperture in the elongated catheter and within a channel of the elongated catheter under negative pressure.

16. The method according to claim 13, wherein the proximal and distal expandable segments are balloons and wherein the step of expanding includes introducing fluid into the balloons.

17. The method according to claim 13, wherein the step of expanding includes positioning the continuous conductive mesh in spaced relation with respect to the occlusion.

18. A tissue treatment apparatus for restoring patency in a body vessel, the tissue treatment apparatus comprising:
    an elongated catheter dimensioned for insertion within a body vessel having an at least partial occlusion, the elongated catheter defining a longitudinal axis and having proximal and distal ends;
    proximal and distal expandable segments mounted to the elongated catheter and being positionable adjacent the occlusion, the proximal and distal expandable segments being adapted to transition from a first contracted condition to a second expanded condition; and
    a mesh in operative engagement with the proximal and distal expandable segments, the mesh being expandable radially outwardly from the catheter upon corresponding transition of the proximal and distal expandable segments to the second expanded condition, the mesh comprising a conductive material adapted to transmit electrosurgical energy to the occlusion, and wherein a maximum outer diameter of the proximal and distal expandable segments is greater than a maximum outer diameter of the mesh to prevent the mesh from contacting the body vessel.

* * * * *